United States Patent
Yu et al.

(10) Patent No.: US 10,506,984 B2
(45) Date of Patent: Dec. 17, 2019

(54) BODY LANDMARK DETECTION BASED ON DEPTH IMAGES

(71) Applicant: Siemens Healthcare GmbH, Erlangen (DE)

(72) Inventors: Lequan Yu, Shatin (HK); Kai Ma, Princeton, NJ (US); Vivek Singh, Princeton, NJ (US); Terrence Chen, Princeton, NJ (US)

(73) Assignee: Siemens Healthcare GmbH, Erlangen (DE)

( * ) Notice: Subject to any disclaimer, the term of this patent is extended or adjusted under 35 U.S.C. 154(b) by 115 days.

(21) Appl. No.: 15/863,138

(22) Filed: Jan. 5, 2018

(65) Prior Publication Data
US 2019/0209098 A1 Jul. 11, 2019

(51) Int. Cl.
*G06K 9/00* (2006.01)
*A61B 5/00* (2006.01)
*G06T 7/00* (2017.01)
*G06T 7/73* (2017.01)

(52) U.S. Cl.
CPC .......... *A61B 5/7267* (2013.01); *A61B 5/0077* (2013.01); *G06T 7/0012* (2013.01); *G06T 7/75* (2017.01); *G06T 2207/10028* (2013.01); *G06T 2207/20081* (2013.01); *G06T 2207/30004* (2013.01)

(58) Field of Classification Search
CPC combination set(s) only.
See application file for complete search history.

(56) References Cited

U.S. PATENT DOCUMENTS

| 10,339,706 B2* | 7/2019 | Black | G06K 9/00369 |
| 2014/0003695 A1* | 1/2014 | Dean | G06T 7/0012 |
| | | | 382/131 |
| 2014/0314290 A1* | 10/2014 | Dabbah | G06T 7/73 |
| | | | 382/131 |

(Continued)

OTHER PUBLICATIONS

Tu, Zhuowen, "Probabilistic Boosting-Tree: Learning Discriminative Models for Classification, Recognition, and Clustering", Integrated Data Systems Departement, Siemens Corporate Research, 8 pp.

(Continued)

*Primary Examiner* — Jose L Couso

(57) ABSTRACT

A system and method includes acquisition of a plurality of sets of body surface data, first data indicating locations of a first one or more body landmarks for each of the plurality of sets of body surface data, and second data indicating locations of a second one or more body landmarks for each of the plurality of sets of body surface data, training, using the plurality of sets of body surface data and data indicating locations of the first one or more body landmarks for each of the plurality of sets of body surface data, of a first reinforcement learning network to identify the first one or more body landmarks based on body surface data, and training, using the plurality of sets of body surface data and data indicating locations of the second one or more body landmarks for each of the plurality of sets of body surface data, of a second reinforcement learning network to identify the second one or more body landmarks based on body surface data.

18 Claims, 6 Drawing Sheets

(56) References Cited

U.S. PATENT DOCUMENTS

| | | | |
|---|---|---|---|
| 2015/0206341 A1* | 7/2015 | Loper | G06T 17/10 |
| | | | 345/420 |
| 2015/0305706 A1* | 10/2015 | Kanik | A61B 8/0883 |
| | | | 600/438 |
| 2017/0091574 A1* | 3/2017 | Udupa | G06T 7/11 |
| 2017/0200272 A1* | 7/2017 | Buisseret | G06T 7/0012 |
| 2017/0270663 A1* | 9/2017 | Hoffmann | A61B 5/02007 |
| 2019/0035149 A1* | 1/2019 | Chen | G06T 15/04 |
| 2019/0108403 A1* | 4/2019 | Smith | G06K 9/00771 |
| 2019/0122424 A1* | 4/2019 | Moore | G06T 17/00 |
| 2019/0213388 A1* | 7/2019 | Makeev | A61B 5/015 |
| 2019/0214135 A1* | 7/2019 | Wu | G06T 7/0014 |
| 2019/0259493 A1* | 8/2019 | Xu | G06K 9/6267 |

OTHER PUBLICATIONS

Levine, Sergey, "Learning Hand-Eye Coordination for Robotic Grasping with Large-Scale Data Collection", Google, 12 pp.

Mnih, Volodymyr et al., "Human-level control through deep reinforcement learning", Letter, Nature, vol. 518, Macmillan Publishers Limited, Feb. 26, 2015, 13 pp.

Sao, Zhe, "Realtime Multi-Person 2D Pose Estimation using Part Affinity Fields", The Robotics Institute, Carnegie Mellon University, Apr. 14, 2017, 9 pp.

Silver, David et al, "Mastering the game of Go without Human Knowledge", Nature, vol. 550, MacMillan Publishers Limited, Oct. 19, 2017, 18 pp.

\* cited by examiner

BODY LANDMARK DETECTION BASED ON DEPTH IMAGES

BACKGROUND

Medical imaging or intervention often relies on an estimation, or model, of a patient upon whom the imaging or intervention is to be performed. For example, position-dependent imaging parameters may differ depending upon the location of a patient's head and torso with respect to an imaging device. Accordingly, a model of the patient is determined prior to imaging in order to conform the imaging parameters to the patient anatomy. The model may include locations of anatomical landmarks, such as shoulders, pelvis, torso, knees, etc.

A model may be determined based on external and/or internal image data. Some conventional systems compare an acquired surface image of a patient against a library of pre-modeled surface images to determine a model corresponding to the patient. The determination may be performed by a neural network which is trained based on the library of pre-modeled surface images.

Conventional modeling techniques may accurately model one portion or segment of the body (e.g., a leg) while failing to accurately model other portions. Conventional techniques also encounter difficulty if a subject patient is disposed in a pose which is not adequately represented in the training library of pre-modeled surface images. What is needed is a system for efficient and suitably-accurate landmark detection based on efficiently-acquired images.

DETAILED DESCRIPTION

The following description is provided to enable any person in the art to make and use the described embodiments and sets forth the best mode contemplated for carrying out the described embodiments. Various modifications, however, will remain apparent to those in the art.

Some embodiments operate to detect body landmarks based on depth images. For example, some embodiments may determine locations of a head, shoulder, torso, knee and ankle based on a two-dimensional depth image. Neural networks may be trained to detect the landmarks automatically, accurately and contemporaneously. Some embodiments may provide suitable landmark detection based on surface data of patient positions and/or anatomies which were not robustly represented in the data used train the networks.

Figure 1:
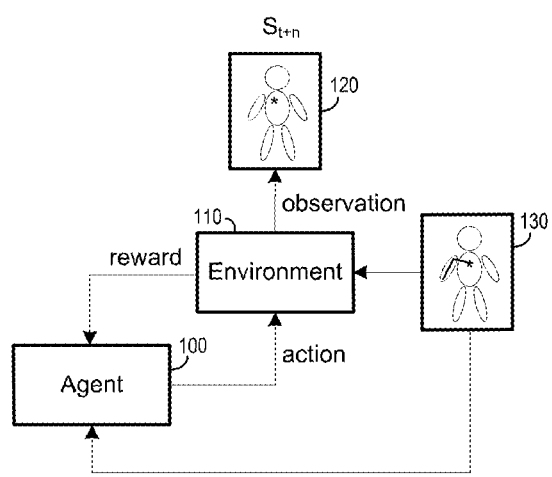
FIG. 1 is a block diagram illustrating training of a network according to some embodiments.

FIG. 1 illustrates training of a Deep Reinforcement Learning (DRL) algorithm according to some embodiments. Agent 100 is generally configured to take actions with respect to environment 110 so as to maximize a cumulative reward. The reward is determined based on an observation 120 of the result of the actions as will be described below. Unlike standard supervised learning techniques, reinforcement learning does not rely on training data consisting of correct input/output pairs, and does not explicitly modify the agent to correct sub-optimal actions.

Generally, agent 100 receives training data 130 and performs an action on environment 110 based on the training data 130. An observation 120 of the effect of the action on environment 110 is determined, as well as an associated reward. Agent 100 performs another action based on the reward (and the observation, in some cases), and the process repeats until a desired observation is achieved. The process generates a control policy for agent 100 which may be applied to unknown data to generate a desired output.

In the particular example of FIG. 1, training data 130 is a depth image of a human body. The depth image is associated with a segment extending from a center of the torso, through the shoulder and to the right wrist of the body. The segment may be determined and associated with the depth image in any suitable manner, including but not limited to manually or by placing markers on the body which appear in the depth image.

Agent 100 receives depth image 130, without the associated segment, and outputs an action. According to some embodiments, the action is a direction from a current pixel of depth image 130, where the initial pixel is located at the center of the torso. Environment 110 determines an observation 120 of the effect of the action, which is a movement of the current pixel in the direction of the action.

The reward is determined based on whether the moved pixel lies along (or within a permissible threshold distance of) the segment of training data 130. If so, a positive reward is provided to agent 100. If not, a negative reward is provided. Learning of the control policy proceeds as described above until the current pixel is located at the end of the segment (i.e., at the right wrist).

For example, it is assumed that a first action is determined as "'Left", and this action is applied to move the current pixel to the left. It is then determined that the moved pixel lies on the segment based on training data 130. Accordingly, a positive reward is provided to agent 100. Next, agent 100 may, based again on the input data, output an action "Left, Up". Conversely, if it was determined that the moved pixel does not lie on the segment, a negative reward may be provided to agent 100. Based on the negative reward and the input data, the next action output by agent 100 may be "Right". Flow continues in this manner until it is determined that the current point is located at the end of the segment. At this time, agent 100 has learned a control policy which will, based on data 130, output a sequence of directions tracing the segment associated with data 130. In embodiments where the segment is constrained to lie completely within the body, the control policy should also conform to this constraint while tracing a path to the destination point.

Figure 2:
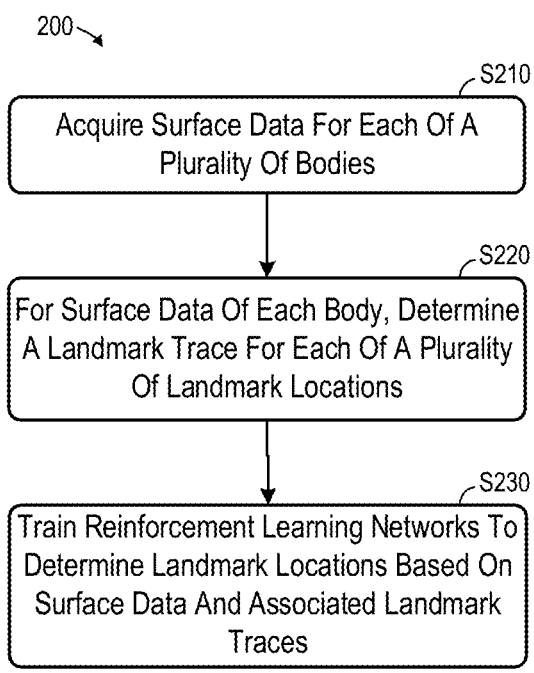
FIG. 2 is a flow diagram of process to train a network according to some embodiments.

FIG. 2 is a flow diagram of process 200 according to some embodiments. Process 200 may be executed to train reinforcement learning networks to determine landmark locations based on input surface data. Process 200 and the other processes described herein may be performed using any suitable combination of hardware, software or manual means. Software embodying these processes may be stored by any non-transitory tangible medium, including a fixed disk, a floppy disk, a CD, a DVD, a Flash drive, or a magnetic tape. Embodiments are not limited to the examples described below.

According to some embodiments, process 200 is executed by a standalone or distributed computing system suitable for training neuron-based networks. Such a system may store training data and may provide interfaces to define the structure of a network to be trained (e.g., including layers, types of layers, nodes and types of nodes) and/or to annotate training data, for example with segment traces.

Initially, surface data of various body poses is acquired at S210. Actual generation of the surface data may be performed by a system which is different from the system used to perform S220 and S230. The surface data may be generated by many remote imaging systems at various times and collected in a data structure (e.g., database, file) from which the surface data is acquired at S210.

According to some embodiments, the surface data may be acquired by a depth camera as is known in the art. A depth camera, mounted in a single stationary position, acquires image data which consists of a two-dimensional image (e.g., a two-dimensional RGB image, in which each pixel is assigned a Red, a Green and a Blue value), and a depth image, in which the value of each pixel corresponds to a depth or distance of the pixel from the depth camera. This image data, consisting of a two-dimensional image and a depth image, will be referred to herein as a two-dimensional depth image.

Figure 3:
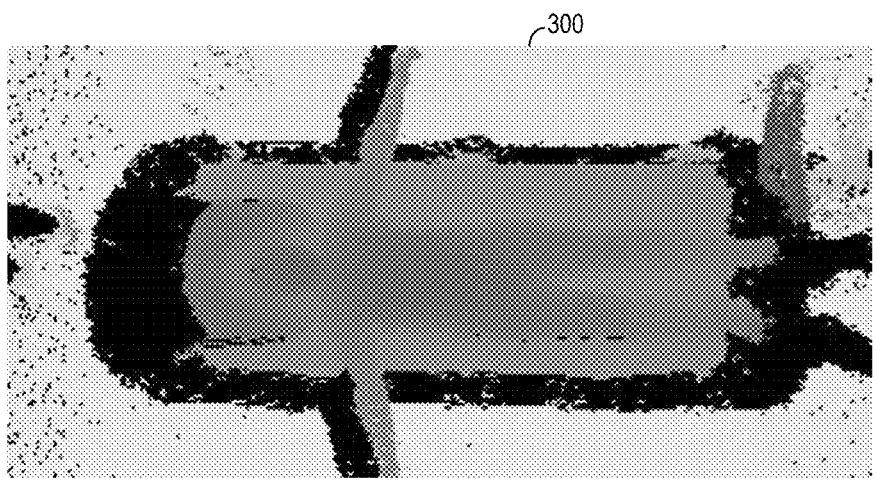
FIG. 3 illustrates a depth image according to some embodiments.
Figure 4:
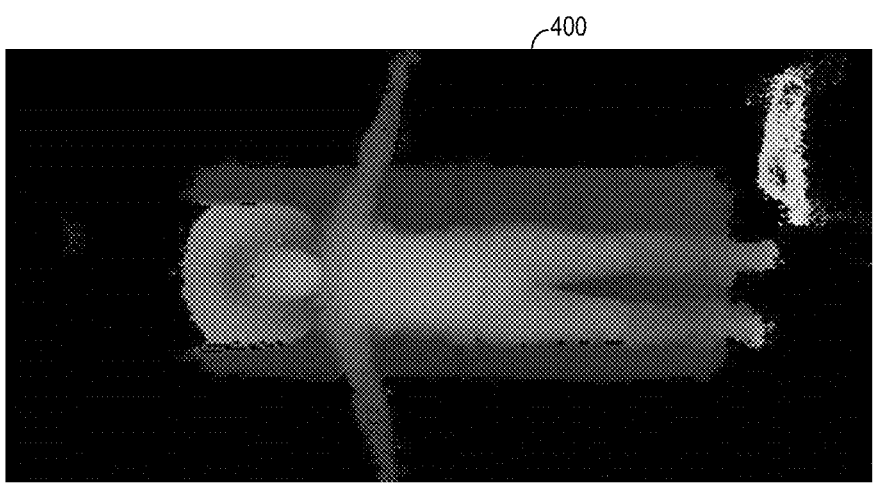
FIG. 4 illustrates a cropped depth image according to some embodiments.

FIG. 3 illustrates two-dimensional image 300 projected from a two-dimensional depth image according to some embodiments. The depth range of the two-dimensional depth image and two-dimensional image 300 is 0.0-3.0 meters in the present example. In view of the fact that the patient lies on a table and exhibits a small range of depths, the original depth image may be cropped to include only pixels within the range of 0.3-1.1 meters. Image 400 of FIG. 4 reflects such cropping according to some embodiments. The surface data acquired at S210 may therefore consist of thusly-cropped images, for each of a variety of bodies and body poses.

Figure 5:
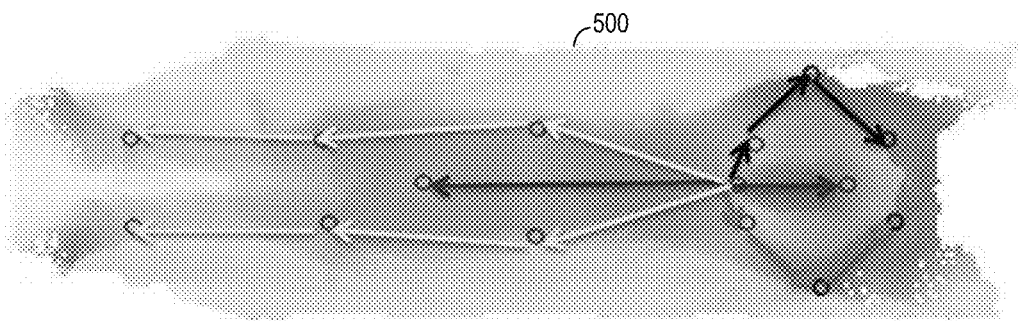
FIG. 5 illustrates a segmented image according to some embodiments.

At S220, and for each body pose, a landmark trace is determined for each of a plurality of landmark locations. The landmark traces are determined based on the acquired surface data of each body pose. FIG. 5 illustrates landmark traces determined for a body pose represented by cropped image 500.

FIG. 5 illustrates annotations of fifteen landmarks (AnkleDn, AnkleUp, KneeDn, KneeUp, Groin, TorsoDn, TorsoUp, ShoulderDn, ShoulderUp, HeadBottom, HeadTop, ElbowDn, ElbowUp, WristDn, WristUp). These annotations may be generated manually or via any suitable landmark detection technique. Each landmark trace proceeds from the HeadBottom landmark through one or more other landmarks, thereby imposing structure constraints among different landmarks associated with a single trace. As will be described below, the landmarks of a single trace may be detected sequentially. This detection may be performed for all traces in parallel since there is no dependence between different tracing paths.

Figure 6:
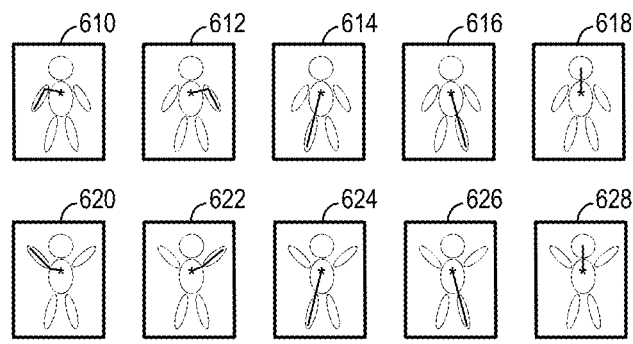
FIG. 6 illustrates ten ground-truth segmented images to train a network according to some embodiments.

FIG. 6 illustrates landmark traces associated with body pose surface data used for network training according to some embodiments. Images 610 through 618 are each associated with a same first set of body pose surface data but with different landmark traces. Images 620 through 628 are each associated with a same second set of body pose surface data but with different landmark traces. The body pose surface data may represent two different human bodies or the same human body. Body pose surface data used for network training may reflect many different body poses and many different bodies.

Figure 7:
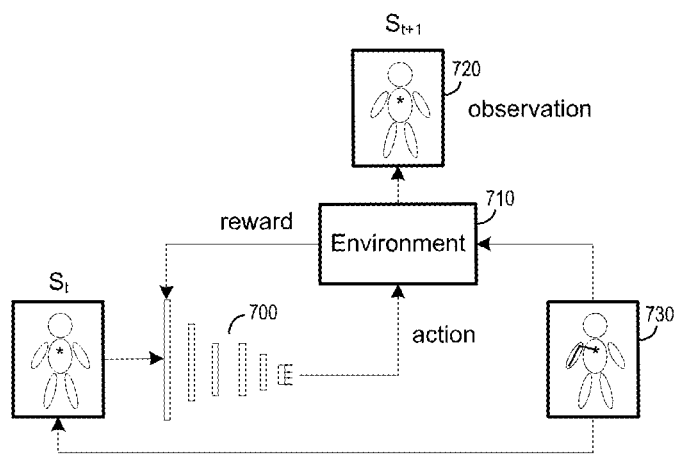
FIG. 7 is a block diagram illustrating training of a network according to some embodiments.

Reinforcement learning networks are trained to determine landmark locations based on the surface data and the associated landmark traces at S230. As illustrated in FIG. 7, network 700 receives training depth image 730, without the associated segment, and outputs an action. Network 700 includes four output neurons, each of which corresponds to a Left, Right, Up or Down action. The output action may correspond to the neuron having a greatest value in response to input image 730.

As described with respect to FIG. 1, the action is a direction from a current pixel of depth image 130, where the initial pixel is located at the center of the torso. Environment 710 determines an observation 720 of the effect of the action, where the effect is a movement of the current pixel in the direction of the action. Environment 710 maintains variables to record the current position of the agent $p_t$ at time step t. The state $s_t$ is an image patch centered at $p_t$. The action $a_t$ is one of four directions that describes the agent's next step.

Environment 710 may determine a reward based on whether the moved pixel lies along (or within a permissible threshold distance of) the segment of training data 130. The reward may be a real value in $[-1,1]$ calculated based on the distance to a landmark location. According to some embodiments, the reward may also be based on whether the current pixel lies within the body, whether the shoulder is reached before the wrist, etc. The reward is provided to network 700 and the process repeats until a control policy is learned. The process is executed with respect to many sets of surface data and associated landmark traces (i.e., landmark traces which trace the same landmarks). For example, network 700 is trained based on image data 610 and 620, and many other sets of image data which include a body surface and a trace of landmarks associated with a right arm.

Network 700 is a Deep Q Network (DQN) according to some embodiments. The goal of S230 is to learn an optimal policy that maximizes cumulative rewards. The process can be formulated as a Markow Decision Process $M:=<S, A, T, R, \gamma>$, where S is a finite set of states, A is a finite set of actions, T is a state transition probability function that describes the probability of arriving in state s' after performing action in state s, R is a reward function that describes the expected reward after a state transition, and $\gamma$ is the discount factor controlling future versus immediate rewards. The total discount future reward may be defined as $G_t = R_{t+1} + \gamma R_{t+2} + \ldots = \Sigma_{k=0}^{\infty} \gamma^k R_{t+k+1}$, and the optimal action-value function $Q^*(s, a) = \max_\pi E(G_t | S_t=s, A_t=a, \pi)$, where $\pi$ is an action policy. The optimal action-value function $Q^*(s, a)$ describes the maximum expected future discounted reward the network can achieve when starting in state s and performing action a. According to the objective of reinforcement learning, the optimal policy may be obtained according to following equation:

$$\pi_*(a \mid s) = \begin{cases} 1, & \text{if } a = \text{argmax}_{a \in \mathcal{A}} q_*(s, a) \\ 0, & \text{otherwise.} \end{cases}$$

However, if the state and action space is very large, it is computationally infeasible to compute Q*(s, a). Therefore, a function approximator may be used to estimate Q*(s, a). Deep neural networks are able to extract compact and representative features from raw pixel images and approximate complex non-linear functions, so a deep neural network (i.e., convolutional neural network) may be used to estimate the optimal action-value function Q(s, a, w)≈Q*(s, a). Q*(s, a) should satisfy the Bellman Equation: Q*(s, a)=$E_{s'}$[r(s, a)+γmax$_{a'}$ Q*(s', a')|s, a], where s' is the possible state after state s. The Deep Q Network may be trained by minimizing the mean square error loss L=(r+γmax$_{a'}$'Q(s', a', w))−Q(s, a, w))$^2$.

Figure 8:
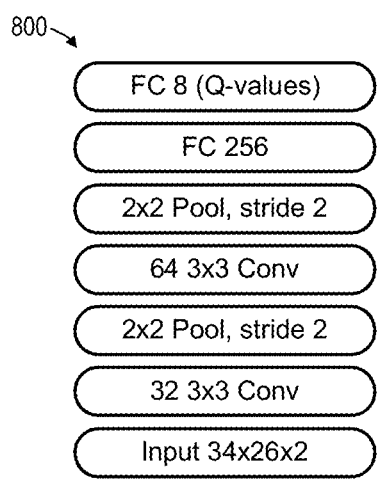
FIG. 8 is a block diagram of a network architecture according to some embodiments.

FIG. 8 is a block diagram of a network architecture according to some embodiments. Network 800 includes convolutional (Cony), pooling (Pool) and fully-connected (FC) layers. According to network 800, the last layer is a fully-connected layer with eight outputs of optimal action-value Q*(s, a). Each output corresponds to one of eight directions, with the highest-value output determining the action which is output by network 800.

Figure 9:
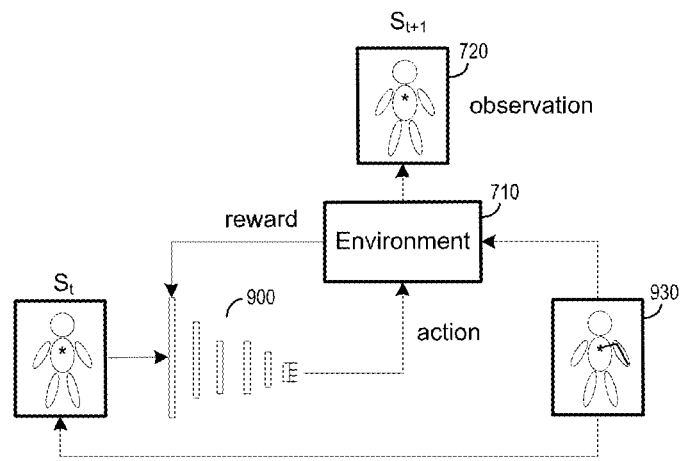
FIG. 9 is a block diagram illustrating training of a network according to some embodiments.
Figure 10:
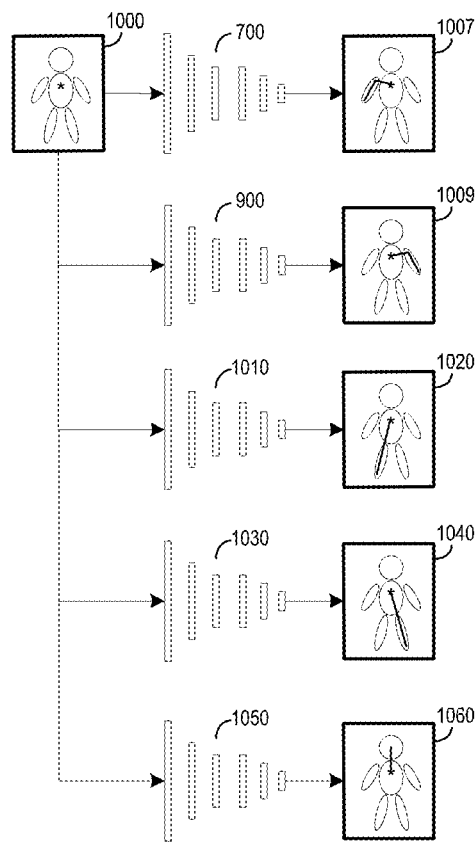
FIG. 10 is a block diagram illustrating usage of five trained networks to output landmark locations according to some embodiments.

FIG. 9 illustrates execution of S230 to train a network with respect to second landmark locations. Network 900 is trained as described above with respect to network 700, although the training is based on sets of image data which include a body surface and a trace of landmarks associated with a left arm. S230 may therefore be executed to train multiple networks independently, where each network is trained to determine landmark locations of a particular trace. According to some embodiments, S230 comprises training five networks to recognize landmarks associated with five different body portions, or segments. FIG. 10 illustrates operation of five such networks according to some embodiments.

As illustrated, each of trained networks 700, 900, 1010, 1030 and 1050 receives surface data 1000 as input. In response, each network outputs a representation of locations of the landmarks which the network was trained to determine. For example, network 700 outputs locations of landmarks associated with a right arm, and network 1000 outputs locations of landmarks associated with a left arm. The output may consist of a trace, of pixel locations, or of any other suitable data to identify landmark locations.

The efficient determination of landmark locations of a person lying on a patient table or hospital bed has a broad range of applications in healthcare. Some examples include long-term monitoring to track patient movement during epileptic seizures, radiation therapy assistance, and scanning workflow improvement.

In some embodiments, surface data is acquired at S210 by an imaging system, landmark traces are determined at S220 by an image processing computer system, and the reinforcement learning networks are trained at S230 by a dedicated and suitable computer system. Each system may be located remote from one another. Even if the system performing S230 receives surface data and landmark traces from other systems, the system performing S230 may also be considered as acquiring the surface data and determining the landmark traces, by virtue of its reception of such data.

Figure 11:
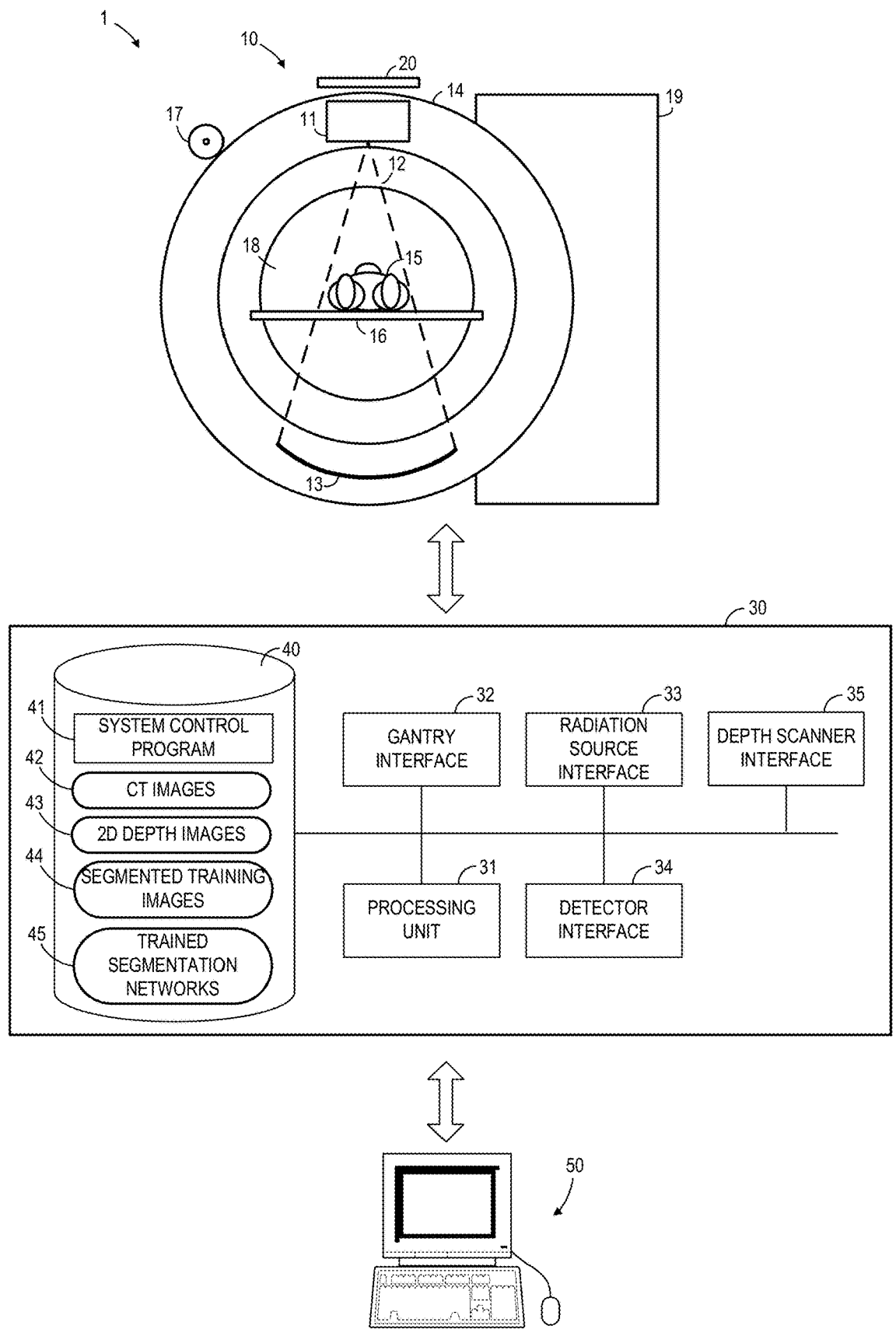
FIG. 11 is a block diagram of a system according to some embodiments.

FIG. 11 illustrates system 1 to execute process 200 and/or to use thusly-trained networks according to some embodiments. Embodiments are not limited to system 1. System 1 includes X-ray imaging system 10, scanner 20, control and processing system 30, and operator terminal 50. Generally, and according to some embodiments, X-ray imaging system 10 acquires two-dimensional X-ray images of a patient volume and scanner 20 acquires surface images of a patient. Control and processing system 30 controls X-ray imaging system 10 and scanner 20, and receives the acquired images therefrom. Control and processing system 30 processes the images. Such processing may be based on user input received by terminal 50 and provided to control and processing system 30 by terminal 50. The processed image may also be provided to a neural network generated according to the present embodiments.

Imaging system 10 comprises a CT scanner including X-ray source 11 for emitting X-ray beam 12 toward opposing radiation detector 13. Embodiments are not limited to CT data or to CT scanners. X-ray source 11 and radiation detector 13 are mounted on gantry 14 such that they may be rotated about a center of rotation of gantry 14 while maintaining the same physical relationship therebetween.

Radiation source 11 may comprise any suitable radiation source, including but not limited to a Gigalix™ x-ray tube. In some embodiments, radiation source 11 emits electron, photon or other type of radiation having energies ranging from 50 to 150 keV.

Radiation detector 13 may comprise any system to acquire an image based on received x-ray radiation. In some embodiments, radiation detector 13 is a flat-panel imaging device using a scintillator layer and solid-state amorphous silicon photodiodes deployed in a two-dimensional array. The scintillator layer receives photons and generates light in proportion to the intensity of the received photons. The array of photodiodes receives the light and records the intensity of received light as stored electrical charge.

In other embodiments, radiation detector 13 converts received photons to electrical charge without requiring a scintillator layer. The photons are absorbed directly by an array of amorphous selenium photoconductors. The photoconductors convert the photons directly to stored electrical charge. Radiation detector 13 may comprise a CCD or tube-based camera, including a light-proof housing within which are disposed a scintillator, a mirror, and a camera.

The charge developed and stored by radiation detector 13 represents radiation intensities at each location of a radiation field produced by x-rays emitted from radiation source 11. The radiation intensity at a particular location of the radiation field represents the attenuative properties of mass (e.g., body tissues) lying along a divergent line between radiation source 11 and the particular location of the radiation field. The set of radiation intensities acquired by radiation detector 13 may therefore represent a two-dimensional projection image of this mass.

To generate X-ray images, patient 15 is positioned on bed 16 to place a portion of patient 15 between X-ray source 11 and radiation detector 13. Next, X-ray source 11 and radiation detector 13 are moved to various projection angles with respect to patient 15 by using rotation drive 17 to rotate gantry 14 around cavity 18 in which patient 15 is positioned. At each projection angle, X-ray source 11 is powered by high-voltage generator 19 to transmit X-ray radiation 12 toward detector 13. Detector 13 receives the radiation and produces a set of data (i.e., a raw X-ray image) for each projection angle.

Scanner 20 may comprise a depth camera. Scanner 20 may acquire depth images as described above. A depth camera may comprise a structured light-based camera (e.g., Microsoft Kinect or ASUS Xtion), a stereo camera, or a time-of-flight camera (e.g., Creative TOF camera) according to some embodiments.

System 30 may comprise any general-purpose or dedicated computing system. Accordingly, system 30 includes processing unit 31 may comprise one or more processors, processing cores, processor threads, etc. configured to execute processor-executable program code to cause system 30 to operate as described herein, and storage device 40 for storing the program code. Storage device 40 may comprise one or more fixed disks, solid-state random access memory, and/or removable media (e.g., a thumb drive) mounted in a corresponding interface (e.g., a USB port).

Storage device 40 stores program code of system control program 41. Processing unit 31 may execute system control program 41 to perform process 200 according to some embodiments. System control program 41 may also or alternatively be executed to move gantry 14, to move table 16, to cause radiation source 11 to emit radiation, to control detector 13 to acquire an image, to control scanner 20 to acquire an image, and to perform any other function. In this regard, system 30 includes gantry interface 32, radiation source interface 33 and depth scanner interface 35 for communication with corresponding units of system 10.

CT images 42 and two-dimensional depth images 43 may be acquired by imaging system 10 and stored in storage device 40. To support the training of networks as described above, depth images may be processed and segmented (i.e., annotated with landmark locations) and stored as segmented training images 44. Trained segmentation networks 45 may be used as described with respect to FIG. 10 to determine landmark locations for associated body segments based on input surface data. Accordingly, system 1 may acquire surface data of patient 15 using scanner 20, submit the surface data to networks 45 to determine landmark locations of patient 15, and control acquisition of CT images of patient 15 based on the determined landmark locations.

Terminal 50 may comprise a display device and an input device coupled to system 30. Terminal 50 may display any acquired images or network output, and may receive user input for controlling display of the images, annotating images, operation of imaging system 10, and/or the processing described herein. In some embodiments, terminal 50 is a separate computing device such as, but not limited to, a desktop computer, a laptop computer, a tablet computer, and a smartphone.

Each of system 10, scanner 20, system 30 and terminal 50 may include other elements which are necessary for the operation thereof, as well as additional elements for providing functions other than those described herein. Embodiments are not limited to a single system performing each of these functions. For example, system 10 may be controlled by a dedicated control system, with the acquired frames and images being provided to a separate image processing system over a computer network or via a physical storage medium (e.g., a DVD).

Those in the art will appreciate that various adaptations and modifications of the above-described embodiments can be configured without departing from the scope and spirit of the claims. Therefore, it is to be understood that the claims may be practiced other than as specifically described herein.

What is claimed is:

1. A system comprising:
   a memory configured to store a plurality of sets of body surface data and, for each set of body surface data, data of a plurality of landmark traces, where each of the plurality of landmark traces is associated with one or more body landmark locations; and
   a processor configured to execute processor-executable program code to:
   train, using the plurality of sets of body surface data and data of a first landmark trace of each of the plurality of sets of body surface data, a first reinforcement learning network to identify a first one or more body landmark locations associated with the first landmark trace, where a result is a trained first reinforcement learning network; and
   train, using the plurality of sets of body surface data and data of a second landmark trace of each of the plurality of sets of body surface data, a second reinforcement learning network to identify a second one or more body landmark locations associated with the second landmark trace, where a result is a trained second reinforcement learning network.

2. A system according to claim 1, wherein the training of the first reinforcement learning network and the second reinforcement learning network is contemporaneous.

3. A system according to claim 1, wherein the processor is further configured to execute processor-executable program code to:
   input a set of surface data associated with a body to the trained first reinforcement learning network;
   input the set of surface data associated with the body to the trained second reinforcement learning network;
   determine, using the trained first reinforcement learning network, a first one or more body landmark locations of the body based on the set of surface data; and
   determine, using the trained second reinforcement learning network, a second one or more body landmark locations of the body based on the set of surface data.

4. A system according to claim 3, further comprising:
   an imaging system to acquire the set of surface data associated with the body.

5. A system according to claim 1, wherein the processor is further configured to execute processor-executable program code to:
   train, using the plurality of sets of body surface data and data of a third landmark trace of each of the plurality of sets of body surface data, a third reinforcement learning network to identify a third one or more body landmark locations associated with the third landmark trace, where a result is a trained third reinforcement learning network.

6. A system according to claim 5, wherein the training of the first reinforcement learning network, the second reinforcement learning network and the third reinforcement learning network is contemporaneous, and wherein the processor is further configured to execute processor-executable program code to:
   input a set of surface data associated with a body to the trained first reinforcement learning network;
   input the set of surface data associated with the body to the trained second reinforcement learning network;
   input the set of surface data associated with the body to the trained third reinforcement learning network;
   determine, using the trained first reinforcement learning network, a first one or more body landmark locations of the body based on the set of surface data;
   determine, using the trained second reinforcement learning network, a second one or more body landmark locations of the body based on the set of surface data; and determine, using the trained third reinforcement learning network, a third one or more body landmark locations of the body based on the set of surface data.

7. A computer-implemented method, comprising:
acquiring a plurality of sets of body surface data, first data indicating locations of a first one or more body landmarks for each of the plurality of sets of body surface data, and second data indicating locations of a second one or more body landmarks for each of the plurality of sets of body surface data;
training, using the plurality of sets of body surface data and data indicating locations of the first one or more body landmarks for each of the plurality of sets of body surface data, a first reinforcement learning network to identify the first one or more body landmarks based on body surface data, where a result is a trained first reinforcement learning network; and
training, using the plurality of sets of body surface data and data indicating locations of the second one or more body landmarks for each of the plurality of sets of body surface data, a second reinforcement learning network to identify the second one or more body landmarks based on body surface data, where a result is a trained second reinforcement learning network.

8. A method according to claim 7, wherein the training of the first reinforcement learning network and the second reinforcement learning network is contemporaneous.

9. A method according to claim 7, further comprising:
inputting a set of body surface data associated with a body to the trained first reinforcement learning network;
inputting the set of surface data associated with the body to the trained second reinforcement learning network;
determining, using the trained first reinforcement learning network, locations of a first one or more body landmarks of the body based on the set of surface data; and
determining, using the trained second reinforcement learning network, locations of a second one or more body landmarks of the body based on the set of surface data.

10. A method according to claim 9, further comprising:
acquiring the set of surface data associated with the body.

11. A method according to claim 7, further comprising:
training, using the plurality of sets of body surface data and data indicating locations of a third one or more body landmarks for each of the plurality of sets of body surface data, a third reinforcement learning network to identify the third one or more body landmarks based on body surface data.

12. A method according to claim 11, wherein the training of the first reinforcement learning network, the second reinforcement learning network and the third reinforcement learning network is contemporaneous, and further comprising:
inputting a set of surface data associated with a body to the trained first reinforcement learning network;
inputting the set of surface data associated with the body to the trained second reinforcement learning network;
inputting the set of surface data associated with the body to the trained third reinforcement learning network;
determining, using the trained first reinforcement learning network, locations of a first one or more body landmarks of the body based on the set of surface data;
determining, using the trained second reinforcement learning network, locations of a second one or more body landmarks of the body based on the set of surface data; and determining, using the trained third reinforcement learning network, locations of a third one or more body landmarks of the body based on the set of surface data.

13. A non-transitory computer-readable medium storing processor-executable process steps, the process steps executable by a processor to cause a system to:
acquire a plurality of sets of body surface data, first data indicating locations of a first one or more body landmarks for each of the plurality of sets of body surface data, and second data indicating locations of a second one or more body landmarks for each of the plurality of sets of body surface data;
train, using the plurality of sets of body surface data and data indicating locations of the first one or more body landmarks for each of the plurality of sets of body surface data, a first reinforcement learning network to identify the first one or more body landmarks based on body surface data, where a result is a trained first reinforcement learning network; and
train, using the plurality of sets of body surface data and data indicating locations of the second one or more body landmarks for each of the plurality of sets of body surface data, a second reinforcement learning network to identify the second one or more body landmarks based on body surface data, where a result is a trained second reinforcement learning network.

14. A medium according to claim 13, wherein the training of the first reinforcement learning network and the second reinforcement learning network is contemporaneous.

15. A medium according to claim 13, the process steps executable by the processor to cause a system to:
input a set of body surface data associated with a body to the trained first reinforcement learning network;
input the set of surface data associated with the body to the trained second reinforcement learning network;
determine, using the trained first reinforcement learning network, locations of a first one or more body landmarks of the body based on the set of surface data; and
determine, using the trained second reinforcement learning network, locations of a second one or more body landmarks of the body based on the set of surface data.

16. A medium according to claim 15, the process steps executable by the processor to cause a system to:
acquire the set of surface data associated with the body.

17. A medium according to claim 13, the process steps executable by the processor to cause a system to:
train, using the plurality of sets of body surface data and data indicating locations of a third one or more body landmarks for each of the plurality of sets of body surface data, a third reinforcement learning network to identify the third one or more body landmarks based on body surface data.

18. A medium according to claim 17, wherein the training of the first reinforcement learning network, the second reinforcement learning network and the third reinforcement learning network is contemporaneous, and wherein the process steps executable by the processor to cause a system to:
input a set of surface data associated with a body to the trained first reinforcement learning network;
input the set of surface data associated with the body to the trained second reinforcement learning network;
input the set of surface data associated with the body to the trained third reinforcement learning network;
determine, using the trained first reinforcement learning network, locations of a first one or more body landmarks of the body based on the set of surface data;

determine, using the trained second reinforcement learning network, locations of a second one or more body landmarks of the body based on the set of surface data; and determine, using the trained third reinforcement learning network, locations of a third one or more body landmarks of the body based on the set of surface data.

\* \* \* \* \*